US008064989B2

(12) United States Patent
Brown et al.

(10) Patent No.: US 8,064,989 B2
(45) Date of Patent: Nov. 22, 2011

(54) PORTABLE OPTICAL COHERENCE TOMOGRAPHY (OCT) DEVICES AND RELATED SYSTEMS

(75) Inventors: William J. Brown, Durham, NC (US); Eric L. Buckland, Hickory, NC (US); Joseph A. Izatt, Raleigh, NC (US)

(73) Assignee: Bioptigen, Inc., Durham, NC (US)

( * ) Notice: Subject to any disclaimer, the term of this patent is extended or adjusted under 35 U.S.C. 154(b) by 558 days.

(21) Appl. No.: 11/535,663

(22) Filed: Sep. 27, 2006

(65) Prior Publication Data

US 2007/0081166 A1 Apr. 12, 2007

Related U.S. Application Data

(60) Provisional application No. 60/721,657, filed on Sep. 29, 2005.

(51) Int. Cl.
*A61B 6/00* (2006.01)
(52) U.S. Cl. ........ 600/476; 600/309; 600/310; 600/407; 356/479; 356/497
(58) Field of Classification Search .................. 600/476, 600/160, 309, 310, 407; 356/479, 497
See application file for complete search history.

(56) References Cited

U.S. PATENT DOCUMENTS

| | | | |
|---|---|---|---|
| 5,921,926 A * | 7/1999 | Rolland et al. | 600/407 |
| 6,230,046 B1 * | 5/2001 | Crane et al. | 600/476 |
| 6,485,413 B1 | 11/2002 | Boppart et al. | |
| 6,763,259 B1 * | 7/2004 | Hauger et al. | 600/427 |
| 7,301,644 B2 | 11/2007 | Knighton et al. | |
| 7,355,716 B2 * | 4/2008 | de Boer et al. | 356/479 |
| 2003/0072007 A1 * | 4/2003 | Fercher | 356/497 |
| 2003/0142934 A1 * | 7/2003 | Pan et al. | 385/116 |
| 2005/0018201 A1 | 1/2005 | de Boer et al. | |
| 2005/0075547 A1 * | 4/2005 | Wang | 600/316 |
| 2005/0140984 A1 * | 6/2005 | Hitzenberger | 356/497 |
| 2005/0171439 A1 | 8/2005 | Maschke | |
| 2005/0249107 A1 * | 11/2005 | Li | 369/275.1 |
| 2007/0002327 A1 | 1/2007 | Zhou et al. | |
| 2007/0081166 A1 | 4/2007 | Brown et al. | |
| 2007/0291277 A1 | 12/2007 | Everett et al. | |

FOREIGN PATENT DOCUMENTS

| | | |
|---|---|---|
| EP | 1 154 224 A1 | 11/2001 |
| WO | WO 99/57507 | 11/1999 |

OTHER PUBLICATIONS

Buckman, A.B., "Analysis of a Novel Optical Fiber Interferometer with Common Mode Compensation", Journal of Lightwave Technology, vol. 7, No. 1, 151-157, Jan. 1989.*

(Continued)

*Primary Examiner* — Brian Casler
*Assistant Examiner* — Daniel Huntley
(74) *Attorney, Agent, or Firm* — Myers Bigel Sibley & Sajovec

(57) ABSTRACT

Portable optical coherence tomography (OCT) devices including at least one mirror configured to scan at least two directions are provided. The portable OCT devices are configured to provide a portable interface to a sample that can be aligned to the sample without repositioning the sample. Related systems are also provided.

27 Claims, 16 Drawing Sheets

OTHER PUBLICATIONS

Pan, Y. et a.l, "Hand-held arthroscopic optical coherence tomography for in vivo high-resolution imaging of articular cartilage", Journal of Biomedical Optics, 8(4), 648-654, Oct. 2003.*

Radhakrishnan S. et al, Real-Time Optical Coherence Tomography of the anterior segment at 1310 nm, Arch Ophthalmol, vol. 119, 1179-1185, Aug. 2001.*

Merriam Webster Online Dictionary Entry for 'integrate'.*

Hoerauf et al., "Transscleral Optical Coherence Tomography—An Experimental Study in Ex-Vivo Human Eyes," Lasers in Surgery and Medicine 30:209-215 (2002).

Radhakrishnan et al., "Real-Time Optical Coherence Tomography of the Anterior Segment at 1310 nm," Archives of Ophthalmology, Aug. 2001, vol. 119, No. 8, pp. 1179-1185.

International Search Report, PCT/US2006/037579, Feb. 16, 2007.

* cited by examiner

PORTABLE OPTICAL COHERENCE TOMOGRAPHY (OCT) DEVICES AND RELATED SYSTEMS

CLAIM OF PRIORITY

The present application claims priority from U.S. Provisional Application No. 60/721,657, filed Sep. 29, 2005, the disclosure of which is hereby incorporated herein by reference as if set forth in its entirety.

FIELD OF THE INVENTION

The present invention relates to imaging and, more particularly, to optical coherence imaging devices and systems.

BACKGROUND OF THE INVENTION

Optical Coherence Tomography (OCT) has been around since the early 1990's and provides a technique for imaging into samples, such as small animals, eyes, tissue, glass and the like. Recent advances have increased the imaging speed, which may allow relatively large image sets (such as 3-D volumes) to be quickly generated Since OCT is high-speed, generally non-contact and non-destructive, it is well suited for imaging dynamics over short time scales, for example, well below 1 second (the beating of a heart tube in a fruit fly) all the way up to changes over a long time scales, for example, days or even longer (tissue growing).

OCT imaging systems are typically divided into several subsystems including an optical engine, a processing unit and a scanning system. The scanning system may provide the interface to the sample that is being imaged. Interfaces to date include attachments to stereo zoom microscopes and table mounted systems for retinal imaging. One retinal imaging interface, for example, Carl Zeiss Meditec's StratusOCT™, looks much like a findus camera. This interface has a chin rest for the patient and a mechanism for aligning the patient with the OCT imaging system. This system typically requires a mobile, upright, and cooperative patient in order to obtain usable OCT images.

SUMMARY OF THE INVENTION

Some embodiments of the present invention provide portable optical coherence tomography (OCT) devices including at least one mirror configured to scan at least two directions. The portable OCT devices are configured to provide a portable interface to a sample that can be aligned to the sample without repositioning the sample.

In further embodiments of the present invention, the portable OCT device may be an OCT probe. The OCT probe may include a relay lens set coupled to the at least one mirror configured to scan at least two directions.

In still further embodiments of the present invention, the OCT probe may be a non-contact probe that does not make physical contact with the sample. The non-contact probe may further include a first relay lens set configured for the non-contact probe. The non-contact probe may be configured to make physical contact with a spacer and the spacer may be configured to make physical contact with the sample.

In some embodiments of the present invention, the OCT probe may be a contact probe configured to make physical contact with the sample. The contact probe may further include a second relay lens set configured for the contact probe. The contact probe may be configured to receive a protective cover on the second relay lens set and the protective cover may be configured to make physical contact with the sample.

In further embodiments of the present invention, the OCT probe may be configured to receive two or more relay lens sets. In certain embodiments, a first of the two or more relay lens sets may be configured for a non-contact probe that does not make physical contact with the sample. A second of the two or more relay lens sets may be configured for a contact probe that makes physical contact with the sample. In further embodiments, a first of the at least two relay lens sets may be configured for imaging through a final optical lensing system external to the probe. A second of the at least two relay lens sets may be configured for imaging without the assist of an optical lensing system external to the probe.

In still further embodiments of the present invention, the OCT probe may further include an integrated reference arm. The OCT probe including the integrated reference arm may further include a beam splitter. The beam splitter may be configured to receive light and provide a portion of the light to an optical path of the reference arm and a remaining portion of the light to the at least one mirror configured to scan at least two directions of an optical path of the sample.

In some embodiments of the present invention, the OCT probe includes a path length adjustment mechanism configured to provide at least two different optical path lengths through the OCT probe. The path length adjustment mechanism may include, for example, a manual adjustment mechanism or a motor driven adjustment mechanism. The motor driven adjustment mechanism may include, for example, a mechanical screw, mechanical sliders and/or a motor driven screw.

In further embodiments of the present invention, the OCT probe may be a portable probe, a probe configured to be mounted on a mechanical boom or a probe configured to be mounted to a head of a user.

In still further embodiments of the present invention, a display may be integrated with the OCT probe. The OCT probe may further include a user interface configured to operate the display and control operation of an OCT engine in communication with the OCT probe.

In some embodiments of the present invention, the OCT probe further includes a partially reflecting element configured to be mounted on a tip of the OCT probe. The partially reflecting element may be configured to serve as a reflection for a common mode-interferometer.

In further embodiments of the present invention, the OCT probe may be configured to generate a reference reflection for a common-mode interferometer based on reflection internal to the sample.

In still further embodiments of the present invention, the OCT probe may further include multi-path delay lines configured to allow extended scan depth multiplexing.

Some embodiments of the present invention provide optical coherence tomography (OCT) systems including an OCT engine and a portable OCT device. The OCT engine includes optics, electronics and/or software configured to acquire data used to generate OCT images of a sample. The portable OCT device is in communication with the OCT engine and includes at least one mirror configured to scan at least two directions. The portable OCT device is configured to provide a portable interface to the sample that can be aligned to the sample without repositioning the sample.

Further embodiments of the present invention provide portable OCT devices comprising an integrated display.

In still further embodiments of the present invention, the portable OCT device may further include a user interface configured to operate the display and control operation of an OCT engine in communication with the portable OCT device. The user interface may include an image acquisition trigger configured to acquire images of the sample and/or controls configured to adjust a scan pattern, a scan range, a scan rate and/or image processing options. The display may be configured to illustrate real time and/or saved images of the sample, system options, system modes and/or system error messages.

In some embodiments of the present invention, the display may be configured to be mounted substantially perpendicular to the side of the portable OCT device, fold out from the side of the portable OCT device or be mounted to the back of the portable OCT device.

Further embodiments of the present invention provide portable OCT devices including an integrated reference arm.

In still further embodiments of the present invention, the OCT probe may include a beamsplitter configured to receive light and provide a portion of the light to an optical path of the reference arm of the portable OCT device and provide a remaining portion of the light to an optical path of the sample. The beamsplitter may be further configured to receive light from the optical path of the reference arm and the optical path of the sample, recombine the light from the optical path of the reference arm and the optical path of the sample and provide the recombined light to an OCT engine in communication with the portable OCT device for processing.

In some embodiments of the present invention, the reference arm may include zero or one or more turning mirrors, one or more focusing lens, zero or one or more dispersion compensation element, zero or one or more attenuation elements and a reflecting mirror.

DETAILED DESCRIPTION OF EMBODIMENTS OF THE INVENTION

Figure 1:
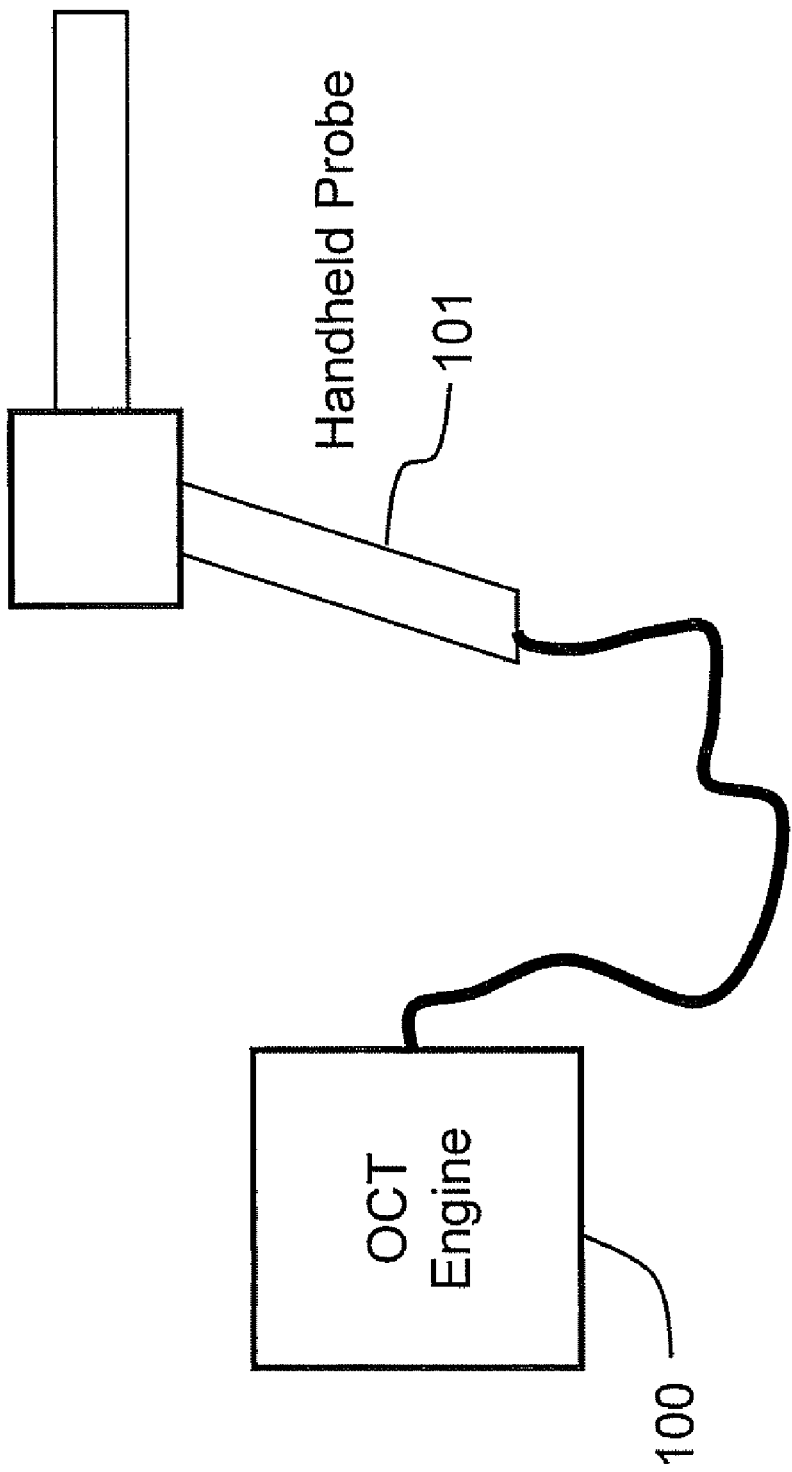
FIG. 1 is a schematic block diagram illustrating an Optical Coherence Tomography (OCT) system including a portable probe according to some embodiments of the present invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will be understood that although the terms first and second are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Some embodiments of the present invention will now be discussed with respect to FIGS. 1 through 16. As illustrated therein, some embodiments of the present invention consist of novel scanning interfaces for Optical Coherence Tomography (OCT) imaging systems. Scanning interfaces according to some embodiments of the present invention are portable and may be portable, thus, the scanner may be aligned with respect to the subject instead of having to align the subject with respect to the scanner. Interfaces according to some embodiments of the present invention may be provided in various configurations, which may include, but are not limited to, a contact probe, a non-contact probe, a non-contact probe with a physical spacer, and the like, the details of which will be discussed further herein.

Conventional implementations of OCT imaging systems typically have a fixed sample interface, where the sample is aligned with the location of the light coming from the OCT system in order to obtain an OCT image. For example, Carl Zeiss Meditec has the StratusOCT™ where the sample interface looks much like a traditional fundus camera with a head and chin rest for the patient. In order to take an image, the patient's head is set in the rest and minor alignment is done to achieve an adequate OCT image. By way of further example, an OCT imaging system may be integrated with a microscope so that the system provides both OCT images of a sample and magnified visual images. The microscope can typically be moved up and down in the Z direction, but the sample is moved in the X and Y directions in order to align it with the OCT system.

For many samples, this configuration of the OCT imaging system works, but there is a whole class of samples where it may be very difficult, or even impossible, to align the sample with respect to the OCT imaging systems. Thus, according to some embodiments of the present invention, the portable probe designs may allow the sample interface portion of the OCT imaging system to be moved around to align it with the sample instead of aligning the sample to the system.

Portable probes, such as handheld probes, according to some embodiments of the present invention may be useful, for example, in retinal and corneal imaging in human patients that are not cooperative or are bedridden; retinal and corneal imaging in infants or children; retinal and corneal imaging in animals including mice, rats, pigs, and monkeys; imaging in confined areas, such as the mouth, ear, and rectum; imaging of samples that do not fit in the microscope; and the like. It will be understood that the uses described herein are provided for exemplary purposes only and, therefore, embodiments of the present invention are not limited to these examples.

Portable probes according to some embodiments of the present invention may be lightweight so that it is can be held, moved and controlled by the user. The OCT system may be relatively compact and, therefore, can be moved from location to location. Current OCT systems are typically fixed in a particular location and the samples or patients must be brought to that location. A portable OCT system according to some embodiments of the present invention can be taken to the samples or patients. This may be particularly useful for, for example, bedridden patients and for animal applications where moving the animals may be difficult on the animals or may increase the chance of infection or contamination. Portable probe OCT imaging systems according to some embodiments of the present invention may be relatively simple and robust with few moving parts and may need little routine alignment or maintenance.

Portable probes according to some embodiments of the present invention can be, for example, contact probes or non-contact probes. A contact probe makes physical contact between the probe and the sample. According to these embodiments of the present invention, alignment may be relatively simple since the tip of the probe can be visually placed on the sample in the desired location for imaging. In some embodiments of the present invention, a protective cover may be provided on the probe, for example, over the end of the probe, in order to reduce the likelihood of contamination of the probe and transfer of material from one sample to another sample. The protective cover may include, for example, glass, plastic or other suitable material, and could be flexible or rigid in design. In some embodiments of the present invention, the protective cover may be disposable or single use, i.e., discarded after one use. However, the protective cover may be reusable without departing from the scope of the present invention. The protective cover may be sterile or capable of being sterilized according to some embodiments of the present invention.

A non-contact probe according to some embodiments of the present does not contact the sample. These embodiments of the present invention may be useful for applications where the patient may not want the probe to physically touch their eye, such as corneal or retinal imaging of conscious humans. Furthermore, non-contact probes may not pose the same contamination issues as the contact probe and the possibility of transfer of material from one sample to another may be reduced. Having some space between the probe tip and the sample may also allow the probe to focus the OCT light to a spot which is advantageous for applications, such as corneal imaging or imaging on or near the surface of a sample.

A contact or a non-contact probe according to some embodiments of the present invention may be configured to image without the assist of an optical lensing system external to the probe. For example, a probe according to some embodiments of the present invention may provide a telecentric scanning system for imaging cornea or other tissue nominally on the exterior surface of a sample.

A contact or a non-contact probe according to further embodiments may be configured to image with the assist of an optical lensing system external to the probe. For example, according to some embodiments of the present invention, a probe may be configured to a non-telecentric scanning system for imaging the retina. In these embodiments, the probe optics may be designed to provide correct imaging of the retina only when proper consideration is taken of the subject cornea and/or lens of the subject eye.

Some embodiments of the present invention provide a spacer in conjunction with a non-contact probe, which may provide a means of controlling the distance between the probe and the sample. For example, the spacer could be attached to the portable probe and could make physical contact with the sample. The spacer may be configured to contact the sample remote from the location where the OCT light shines on the sample. For corneal imaging, the spacer could be circular in design so that it fits around the eye of the patient. This may allow the user to align the probe with the patient, without having anything touch the patient's eye, which may be desirable. According to some embodiments of the present invention, the spacer could have slots or openings or could be optically clear so that the user can look through the spacer to see where the probe is aligned. Embodiments of the present invention including a spacer could also be useful for imaging systems where the OCT light is focused as it leaves the probe. It is important to control the distance between the probe and the sample since there is a fairly narrow depth over which OCT imaging occurs and that location in depth needs to be aligned with the surface or just below the surface of the sample. The spacer may be disposable or reusable without departing from the scope of the present invention.

Typical OCT imaging systems generally use light that is infrared or near infrared and, therefore, may be difficult or impossible for a user to see. Adding some visible light in the OCT engine that co-propagates with the OCT light may allow the user to see where the OCT image is being acquired on the sample. This visible light may be referred to as an aiming beam and may be generated, for example, by a laser or any other light source in the visible wavelength range. This aiming beam may be used in conjunction with any of the embodiments of the present invention discussed herein without departing from the scope of the present invention. For example, the aiming beam may be useful in conjunction with non-contact embodiments of the present invention discussed herein, where the user may not know exactly where on the sample the OCT image is being acquired.

Figure 2:
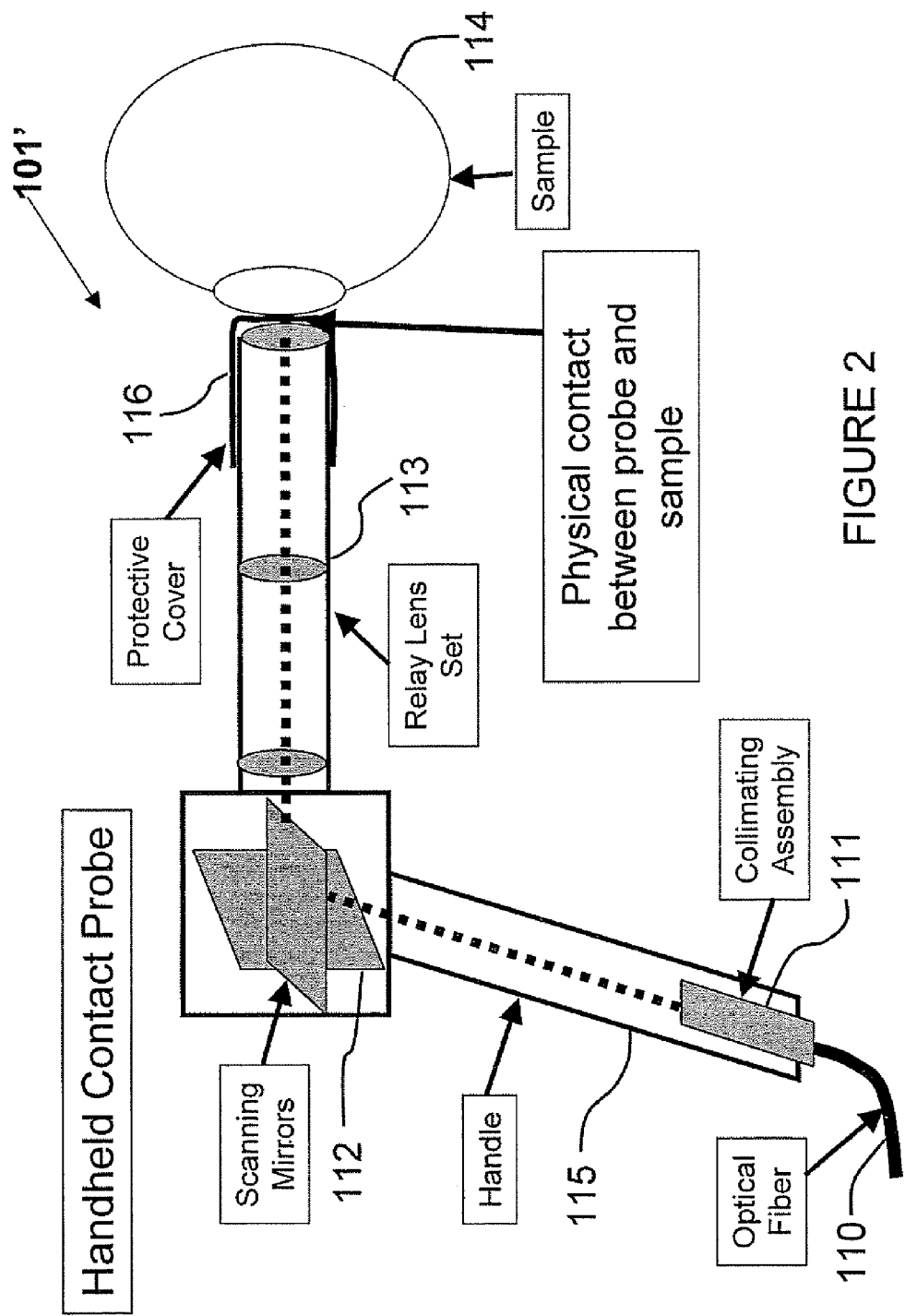
FIG. 2 is a schematic block diagram illustrating a contact portable probe according to some embodiments of the present invention.
Figure 3:
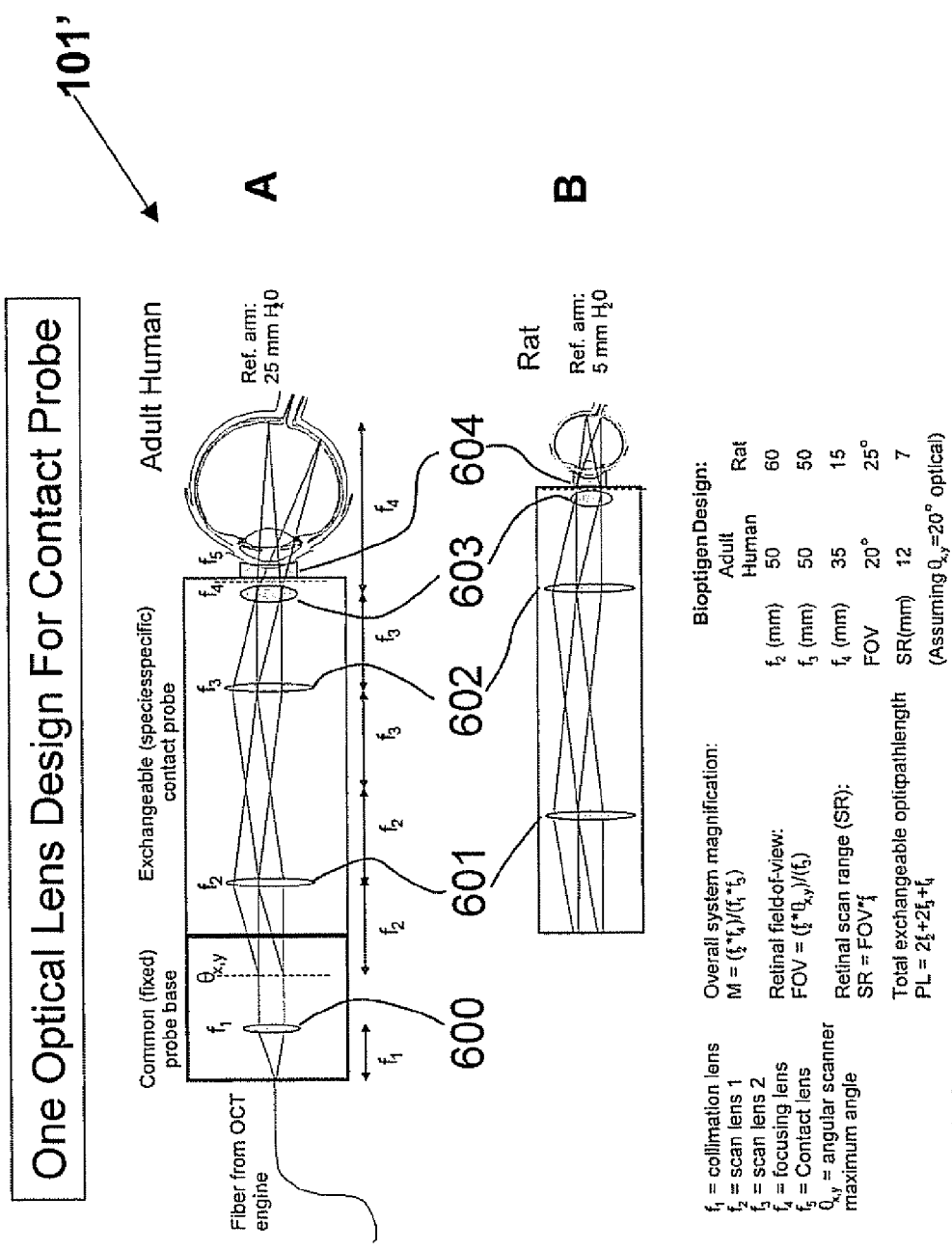
FIGS. 3A and 3B are schematic block diagrams illustrating optical lens set configuration of the portable probe of FIG. 1 according to some embodiments of the present invention.

Various embodiments of the present invention will now be discussed with respect to FIGS. 1 through 16. Referring first to FIGS. 1 through 3, contact probes according to some embodiments of the present invention will be discussed. As illustrated in FIG. 1, systems may include an OCT engine 100 connected to a portable probe 101. The OCT engine 100 may include the optics, electronics and/or software used to acquire the data used to generate OCT images. The portable probe 101 provides an interface to the sample.

FIG. 2 illustrates various components of portable probes 101' according to some embodiments of the present invention. Light enters along an optical fiber 110 from the OCT engine (not shown, 100 of FIG. 1). Light exits the fiber and passes through a collimating assembly 111 at the base of the handle 115. Once collimated, the light is redirected by one or more scanning mirrors 112 and continues through a relay lens set 113 to the sample 114. Light is scattered from the sample 114 and passes back through the portable probe 101' to the optical fiber 110 and on to the OCT engine (not shown).

As illustrated in FIG. 2, there is physical contact between the end of the portable probe 101' and the sample 114. As discussed above, in some embodiments of the present invention, an optional protective cover 116 may be provided over the probe 101'. The protective cover 116 may be disposable or reusable without departing from the scope of the present invention. The protective cover 116 may be sterilized or sterilizable.

Referring now to FIGS. 3A and 3B, optical paths through the portable probe 101' and potential configurations for different probes that are suitable for different applications will be discussed. There may be several lenses in the optical system, for example, the collimating lens 600, two scan lens 601 and 602, the focusing lens 603 and the contact lens 604. It will be understood that the portable probe 101' of FIGS. 3A and 3B is provided for exemplary purposes only and that embodiments of the present invention are not limited to this configuration. For example, other optical lens train designs may be used having fewer or more than five lenses without departing from the scope of the present invention. It will be understood that the focal lengths of the various lenses may vary based on the type of sample. For example, the focal lengths given in FIGS. 3A and 3B are for a human eye sample and a rat eye sample, respectively.

Figure 4:
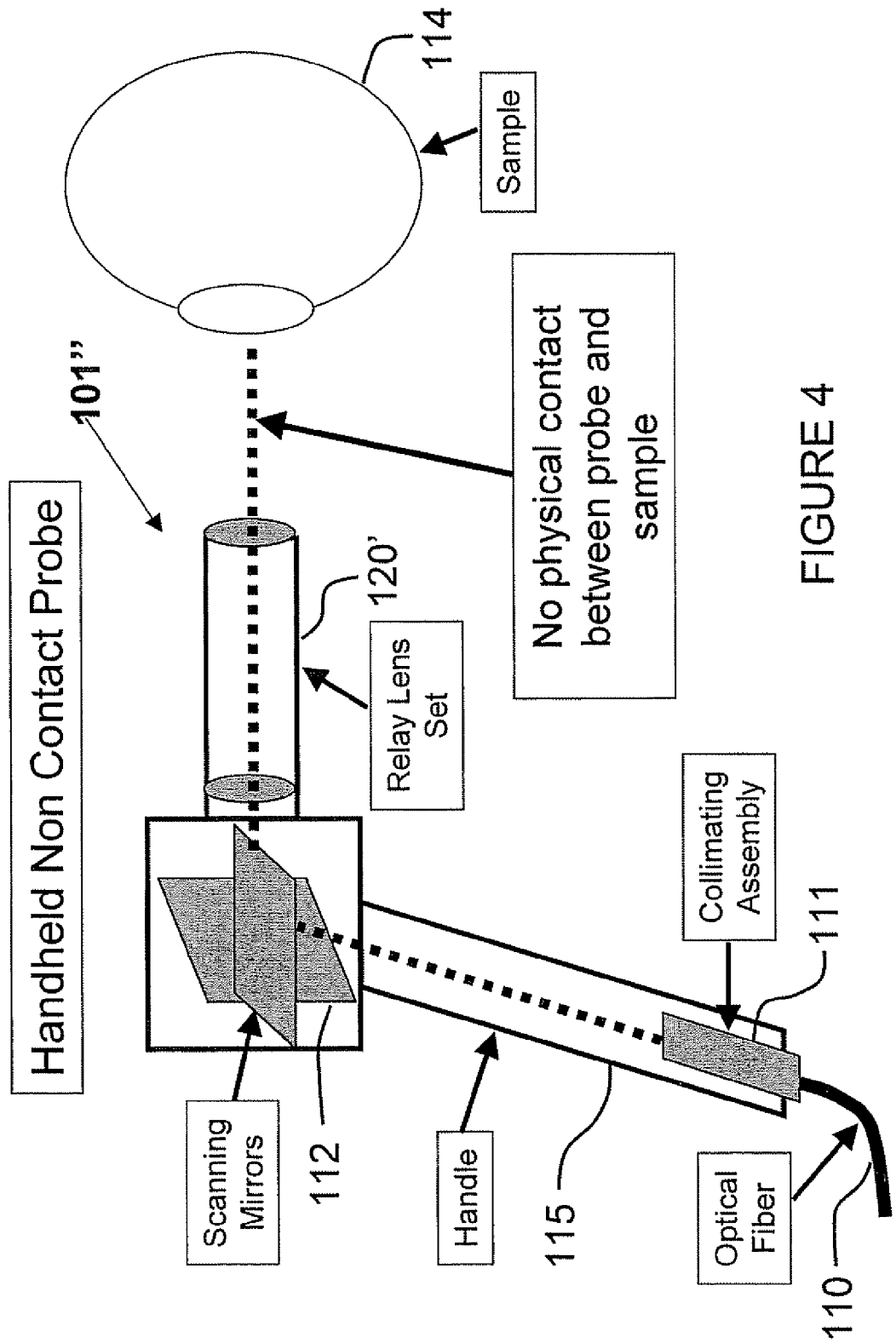
FIG. 4 is a schematic block diagram illustrating a non-contact portable probe for use in OCT systems according to some embodiments of the present invention.

Referring now to FIG. 4, portable non-contact probes 101" according to some embodiments of the present invention will be discussed. As illustrated in FIG. 4, the non-contact probe 101" is similar to the contact probe 101' illustrated in FIG. 2, however, the non-contact probe 101" does not actually touch the sample 114. Accordingly, in these embodiments of the present invention the relay lens set 120' may be different than the relay lens set 120 for the contact probe 101'.

As discussed above, the light enters the non-contact probe 101" from an optical fiber 110 and passes through a collimating assembly 111 at the base of the handle 115. From there the light is steered by the scanning mirrors 112, passes through the relay lens set 120', and is incident on the sample 114. Light is scattered back by the sample 114 and retraces its path through the non-contact probe 101" before returning to the optical fiber 110

As discussed above, the non-contact probe 101" may have a different relay lens set than the contact probe 101. For example, the optical lens set of the non-contact probe may be configured as shown in FIGS. 6A and 6B. As illustrated therein, the optical lens train system may include a collimating lens 650 and multiple scan lenses 651 and 652. Depending on the sample, additional lenses may be used. As shown in FIG. 6A for a corneal application 660, a focusing lens 653 is used to focus the light onto the sample. As shown in FIG. 6B, in retinal scanning applications the light is collimated when it hits the sample 114 and is focused by the lens in the eye of the sample 114.

Figure 5:
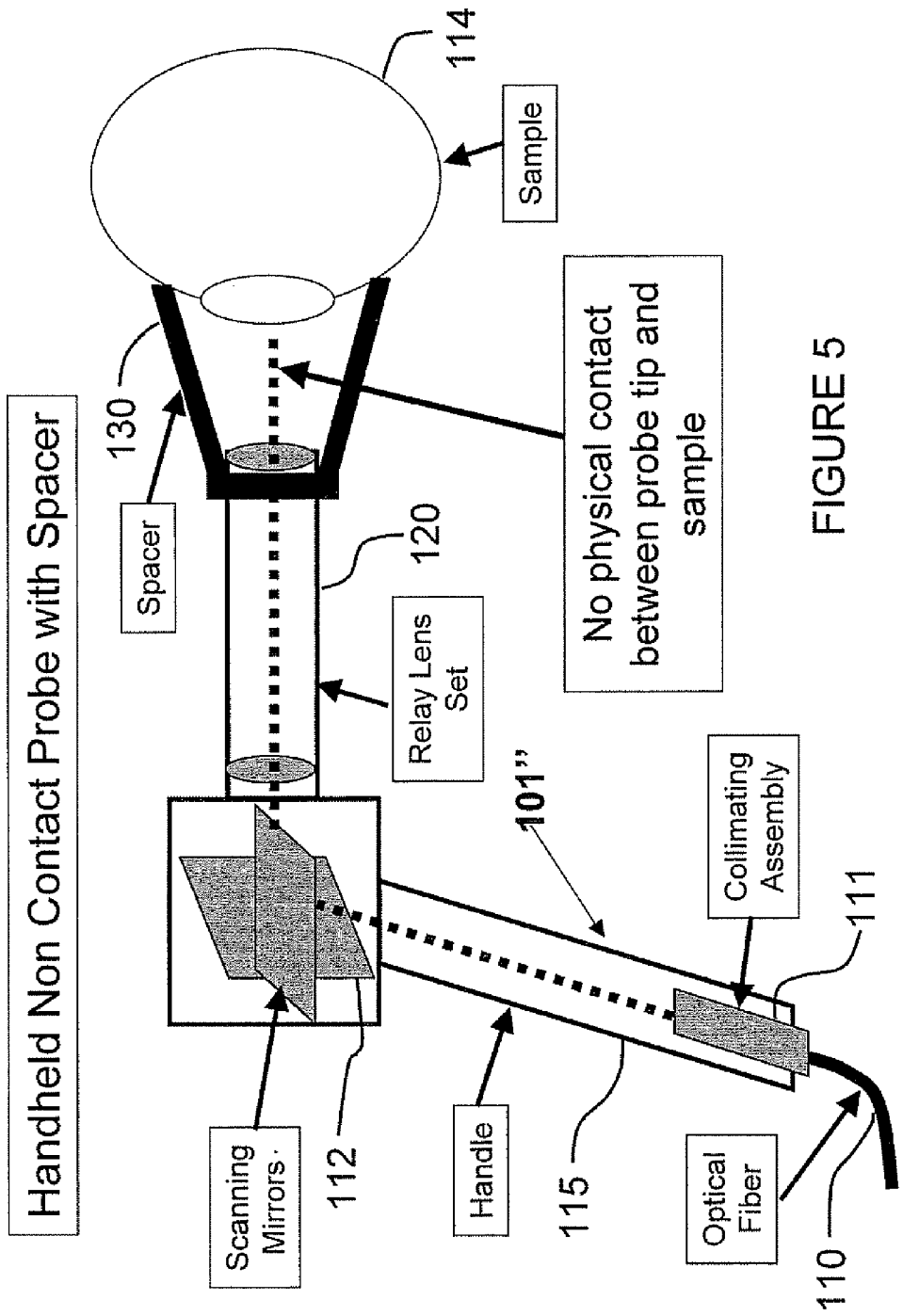
FIG. 5 is a schematic block diagram illustrating a non-contact portable probe used in conjunction with a spacer according to some embodiments of the present invention.
Figure 6:
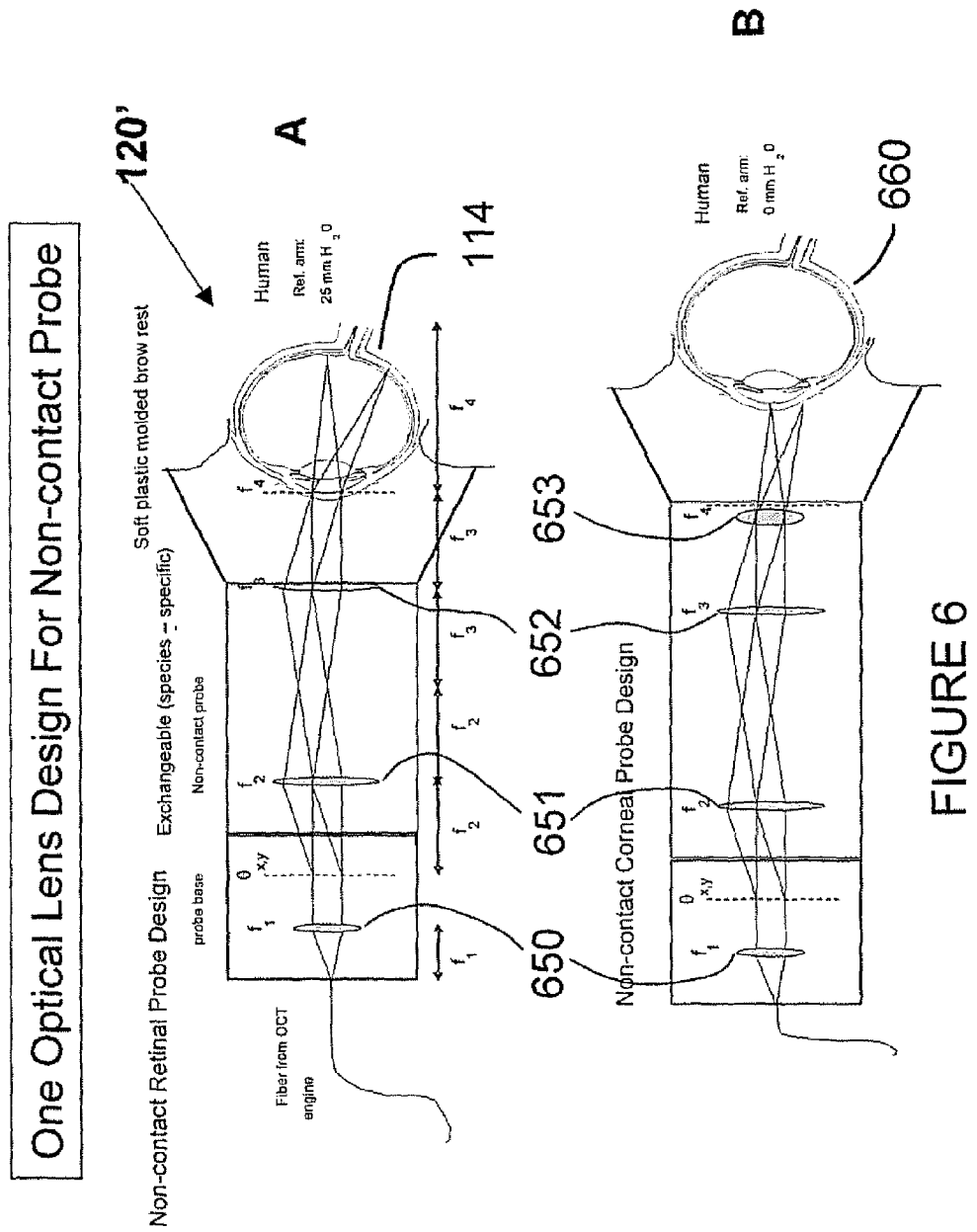
FIGS. 6A and 6B are schematic block diagrams illustrating optical lens sets for use in the non-contact portable probe in FIGS. 4 and 5 according to some embodiments of the present invention.

Referring now to FIG. 5, non-contact probes according to further embodiments of the present invention will be discussed. As illustrated in FIG. 5, the non-contact probe 101" is used in conjunction with a spacer 130 at the end of the portable probe 101". The spacer 130 contacts the sample 114 remote from the location where the light passes from the probe 101" to the sample 114. The spacer 130 may allow the user to align the portable probe 101" with the sample 114 and hold the probe 101" steady relative to the sample 114 while not actually touching the sample where the OCT image is being taken as that location may be particularly sensitive, for example, when the sample 114 is an eye. The non-contact probe 101" of FIG. 5 used in conjunction with the spacer 130 may use the same relay lens set 120' as the non-contact probe 101" of FIG. 4, for example, the relay lens set 120' of FIGS. 6A and 6B. As discussed above, in some embodiments of the present invention, the spacer 130 may have holes or slots or be transparent or partially transparent in nature so that the user can see through the spacer to facilitate alignment of the OCT light with the desired location on the sample 114.

Figure 7:
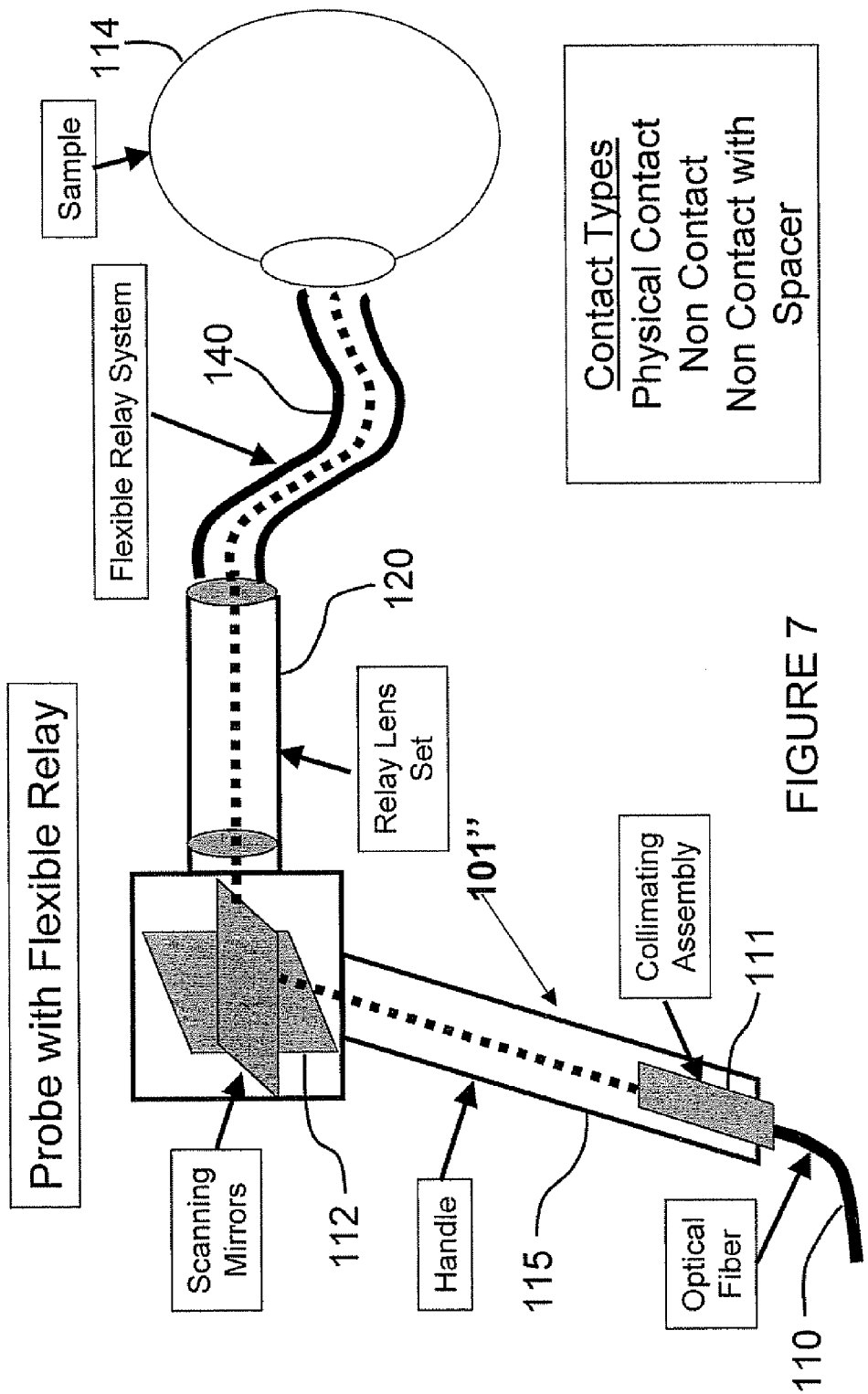
FIG. 7 is a schematic block diagram illustrating a portable probe used in conjunction with a flexible relay according to some embodiments of the present invention.

Referring now to FIG. 7, a non-contact probe 101" used in conjunction with a flexible relay system 140 according to some embodiments of the present invention will be discussed. The flexible relay system may carry both the light from the relay lens set 120' to the sample 114 and the light coming back from the sample 114. This flexible relay system 140 may be implemented using, for example, fiber optics or a multi-lens system in a flexible mechanical package. The fiber optic implementations could be one or more single mode fibers, one or more multimode fibers and/or one or more fibers with multiple cores (single mode or multimode) in each fiber.

Figure 8:
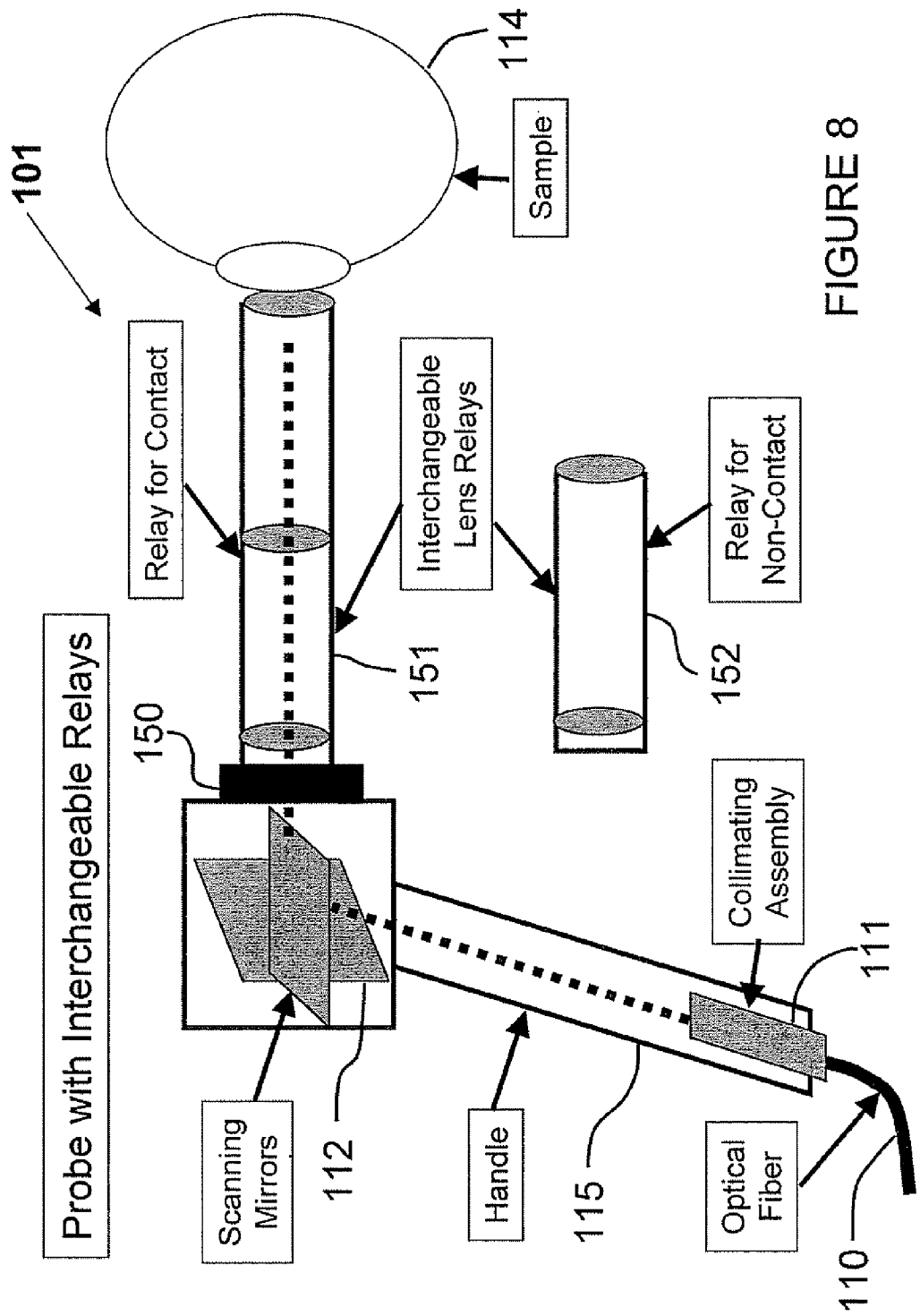
FIG. 8 is a schematic block diagram illustrating a portable probe including interchangeable lens sets according to some embodiments of the present invention.

Referring now to FIG. 8, portable probes including interchangeable lens relays according to some embodiments of the present invention will be discussed. The interchangeable relays may be used in conjunction with contact 101' or non-contact 101" probes (which will be referred to collectively herein as probe 101) according to some embodiments of the present invention. In other words, a single portable probe 101 may be configured to switch between contact mode and non-contact mode by replacing the corresponding relay lens set 151 and 152, respectively. As illustrated in FIG. 8, one or more relay lens sets 151, 152 can be connected to the same portable probe 101. A common interface 150 is used to allow the relay lens sets 151, 152 to connect to the portable probe 101. These embodiments of the present invention may allow the user to switch between types of samples or images by swapping out the relay lens set 151, 152 on the portable probe. In some embodiments of the present invention, the system may be configured to recognize a particular relay lens set and set up the rest of the system to accommodate that particular relay lens set. This may be done automatically upon connection of the relay lens set.

Various embodiments of portable probes will now be discussed with respect to FIGS. 9 through 16. It will be understood that although FIGS. 9 through 16 illustrate specific probe embodiments, for example, contact or non-contact probes, embodiments of the present invention are not limited to this configuration. The features of the embodiments discussed with respect to FIGS. 9 through 16 may be used in combination with any embodiment of the portable probe without departing from the scope of the present invention.

Figure 9:
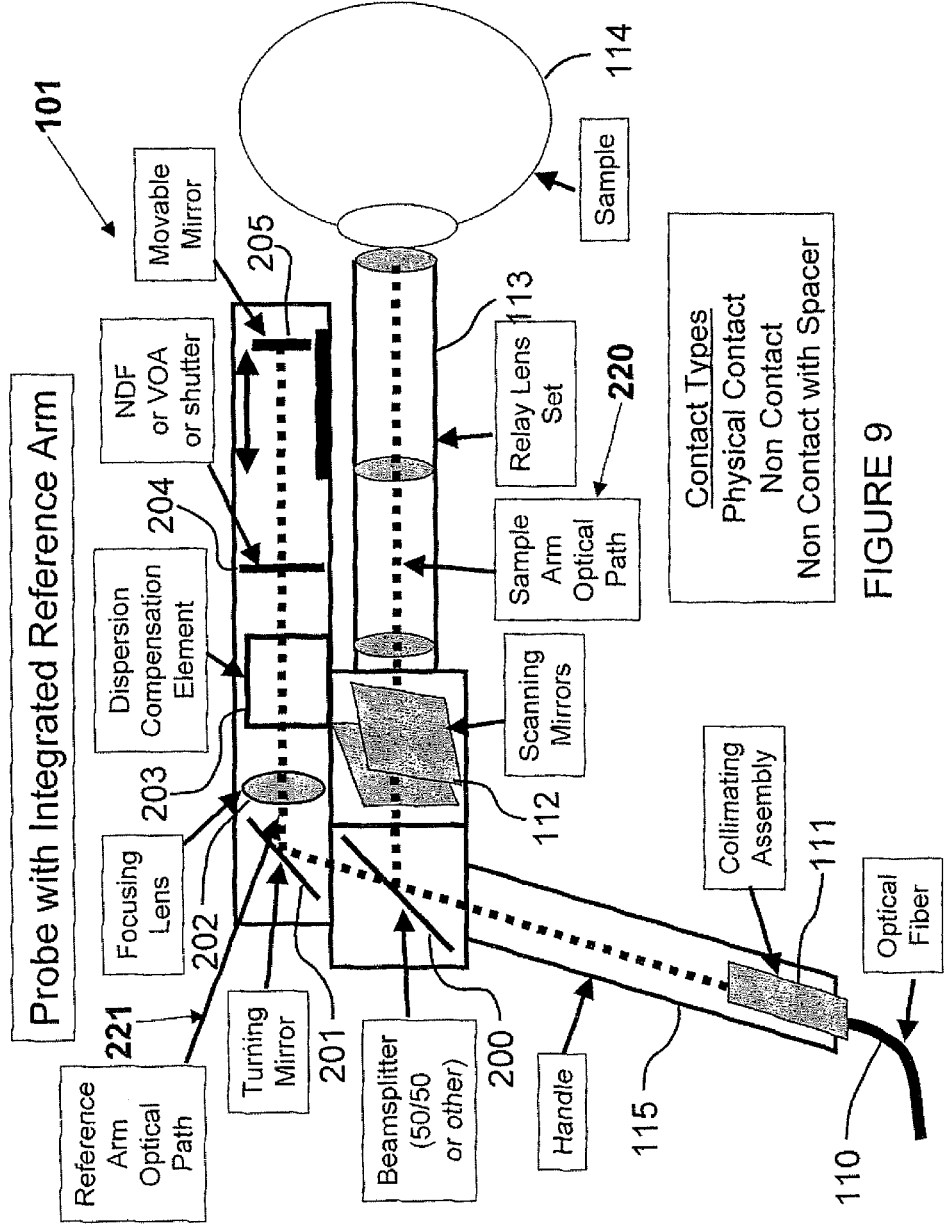
FIG. 9 is a schematic block diagram of illustrating a portable probe integrated with a reference arm according to some embodiments of the present invention.

Referring now to FIG. 9, portable probes having integrated reference arms according to some embodiments of the present invention will be discussed. As illustrated in FIG. 9, the portable probe includes a reference arm, which generally resides in the OCT engine (not shown). The light enters the portable probe 101 through an optical fiber 110, passes through a collimating assembly 111 at the base of the handle 115 and is incident on a beamsplitter 200. The beamsplitter 200 sends some of the light to the sample arm optical path 220 and the rest of the light passes on to the reference arm optical path 221. The ratio of the beamsplitter can be any realizable value. In some embodiments of the present invention, more light will go through the sample arm optical path 220 than through the reference arm optical path 221. In the sample arm optical path 220, the light is directed by the scanning mirrors 112, passes through a relay lens set 113, and onto the sample 114. Light scattered back by the sample 114 follows the sample arm optical path 220 in reverse back to the beamsplitter 200.

The rest of the light from the beamsplitter 200 passes to the reference arm optical path 221, which consists of zero, one, or more turning mirrors 201, one or more focusing lenses 202, zero, one, or more dispersion compensation elements 203, zero, one, or more attenuation elements 204, and a reflecting mirror 205. The reflecting mirror 205 sends light back down the reference arm optical path 221 to the beamsplitter 200. The dispersion compensating elements 203 are optional and may be used in cases where the dispersion in the reference path 221 needs to be closely matched to the dispersion in the sample path 220. The attenuation elements 204 are also optional and may reduce the power level returning from the reference arm 221 if there is too much power. The reflecting mirror 205 may or may not be movable to allow adjustment of the reference arm path length. This adjustment may be done manually by the user or automatically by the OCT system without departing from the scope of the present invention.

Once the light from the sample and reference arms reach the beamsplitter 200 it is recombined and passes through the collimating assembly 111 and back into the optical fiber 110. From this point it returns to the OCT engine (not shown) for acquisition and processing.

Embodiments of the present invention illustrated in FIG. 9 may be relatively insensitive to changes in the optical fiber 110 that connects the OCT engine (not shown) to the portable probe 101. Furthermore, these embodiments may allow the user access to the reference arm and the elements in the reference arm. This may be particularly useful if the elements in the reference arm need to be periodically adjusted or modified for different samples. The user can easily swap out components in the reference arm, such as the dispersion compensation elements 203, or modify an element for example, change the attenuation introduction by the shutter 204 or the optical path length of the reference by changing the mirror location 205.

Figure 10:
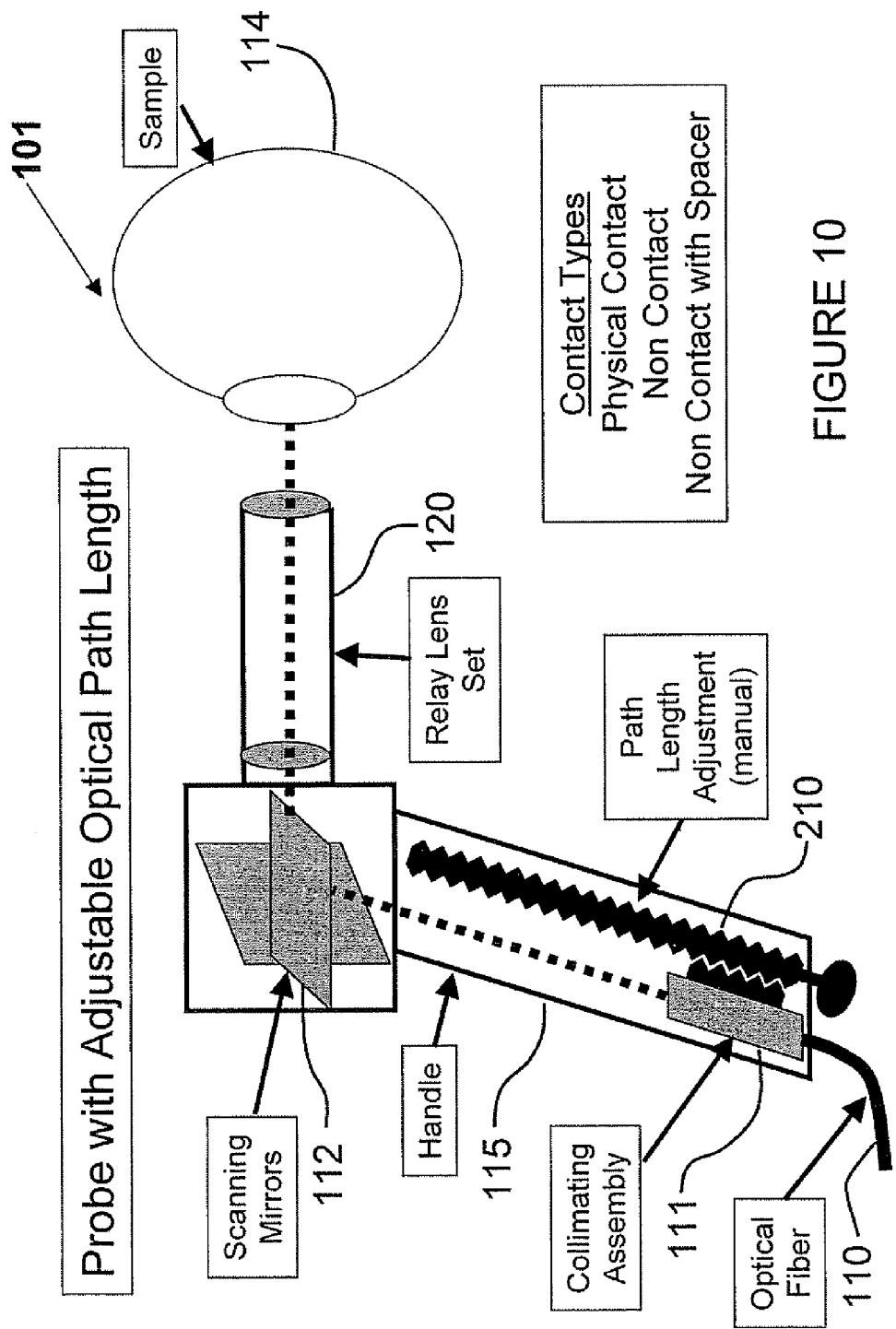
FIG. 10 is a schematic block diagram illustrating a portable probe having an adjustable optical path length according to some embodiments of the present invention.

Referring now to FIG. 10, probes with adjustable optical path lengths according to some embodiments of the present invention will be discussed. As illustrated in FIG. 10, the portable probe 101 has a path length adjustment mechanism 210 for the collimating assembly 111. This path length adjustment mechanism 210 may allow the user to change the optical path length through the portable probe 101 to compensate for other variations in path length either in the OCT engine 100 (FIG. 1) or in the sample 114. In embodiments of the present invention illustrated in FIG. 10, the path length adjustment mechanism 210 may be a motor driven adjustment mechanism, such as a mechanical screw that is driven by a knob at the base of the handle 115 illustrated in FIG. 10, however, embodiments of the present invention are not limited to this configuration. For example, mechanical sliders and motor driven screws may be used in place of the mechanical screw. It will be understood that the optical path length may be adjusted at other locations in the probe or by other mechanisms, such as electro-optic devices whose index of refraction may be altered by applying an electric field across the optical material and, therefore, path length adjustment mechanisms are not limited by the examples discussed herein.

Figure 11:
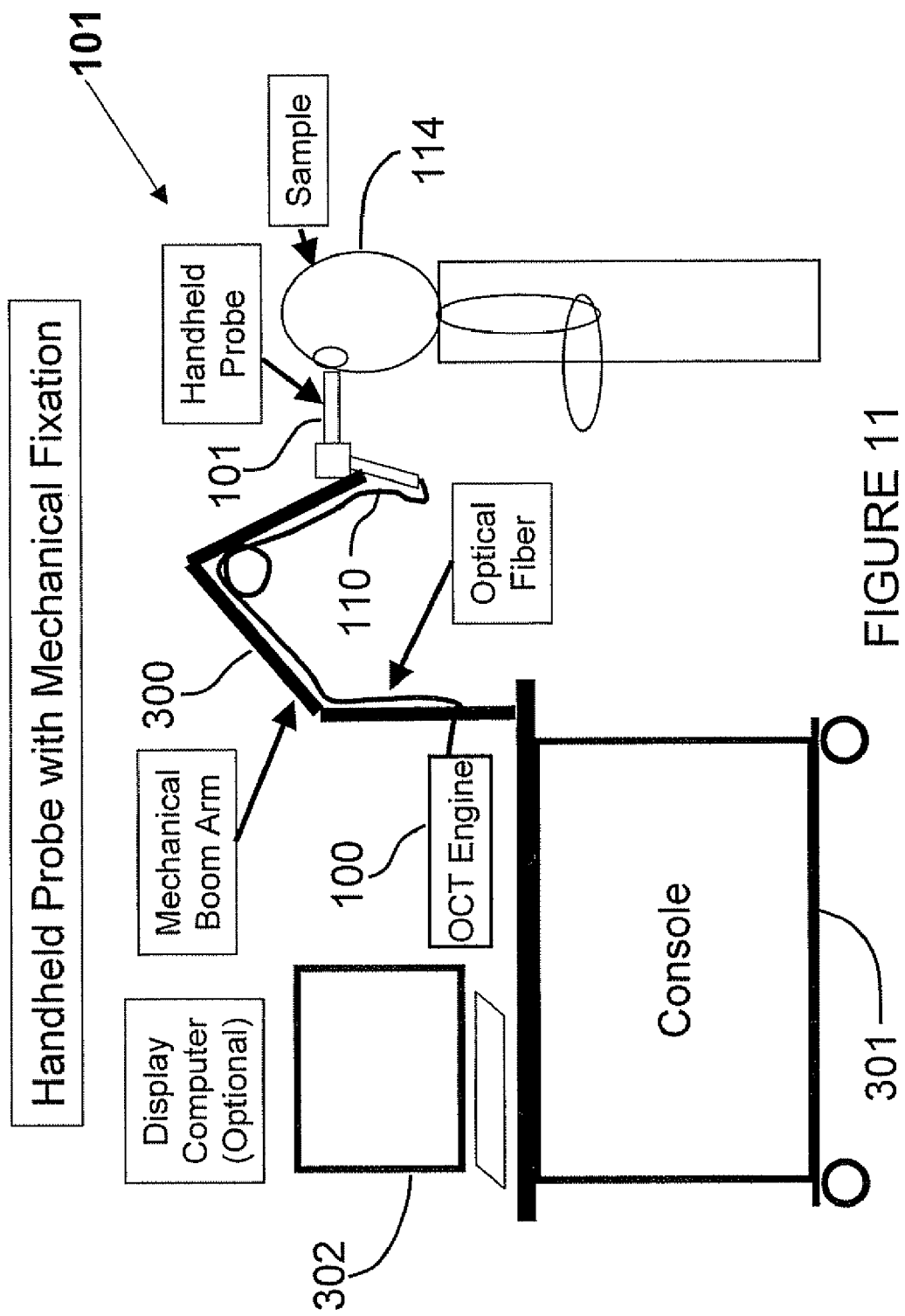
FIG. 11 is a schematic block diagram illustrating a portable probe for use in OCT systems according to some embodiments of the present invention.

Referring now to FIG. 11, a portable probe including a mechanical fixation according to some embodiments of the present invention will be discussed. As illustrated in FIG. 11, the portable probe 101 is mounted on a mechanical boom arm 300 that is fixed to a base or console 301. The mechanical boom arm 300 provides a way to align the portable probe 101 with the sample 114 without the user having to hold the probe. A lightweight, easy to move probe is used to simplify moving and fixing the probe relative to the sample. In embodiments of the present invention illustrated in FIG. 11, the mechanical boom arm 300 is mounted to a console 301 that contains the OCT engine 100 and a display computer 302. Some embodiments of the present invention may include an independent cart for the mechanical boom arm or a console that only has the OCT engine 100 and not the display computer 302. The mechanical boom arm 300 may be counterbalanced so that it is easy to move and easy to fix in a given position. In some embodiments of the present invention, the mechanical fixation could be used in conjunction with holders or fixation mechanisms for the sample. For example, a chin rest could be mounted to the console 301 and the patient's head could be placed on the chin rest and the portable probe moved to align with the patient's eye. The probe could also be rotated to a vertical configuration and samples could be placed on the console 301 or on another surface. In some embodiments of the present invention, the console may have wheels to facilitate moving the OCT system between locations instead of bringing the samples to the OCT system.

Figure 12:
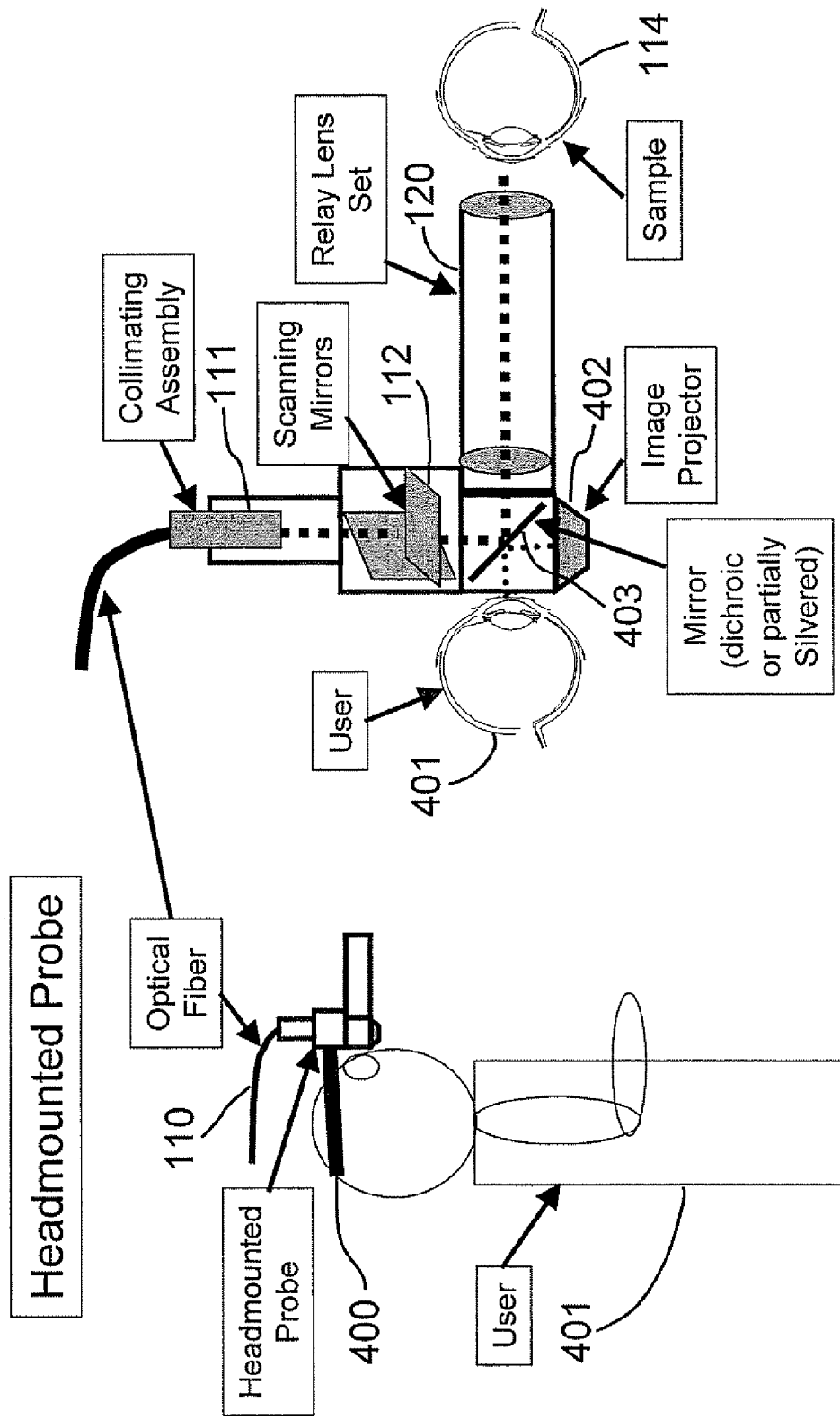
FIG. 12 is a schematic block diagram illustrating a head mounted probe for use in OCT systems according to some embodiments of the present invention.

Referring now to FIG. 12, a headmounted probe according to some embodiments of the present invention will be discussed. As illustrated in FIG. 12, portable probe is reconfigured so that it can be headmounted 400 by the user 401. The light enters the headmounted probe 400 via an optical fiber 110 and passes through a collimating assembly 111. From there the light bounces off the scanning mirrors 112 and then the partial mirror 403. This mirror 403 can be, for example, partially silvered or a dichroic that reflects in the wavelength range of the light from the OCT engine and transmits in the visible wavelength region. The purpose of the partial mirror 403 is to allow the user to look down the path traveled by the OCT light and, thus, may simplify alignment with the sample.

After the partial mirror 403, the light passes through a relay lens set 120 and onto the sample. Light scattered by the sample returns back along the same path until it is reaches the optical fiber 110 and goes back to the OCT engine. As an option an image projector 402 can be used to display an image for the user 401. This image could be the OCT image from the sample 114 or information regarding the setup and state of the OCT system. The head mounted probe 400 may be lightweight so that it can be easily worn by the user without slipping or inducing fatigue.

Figure 13:
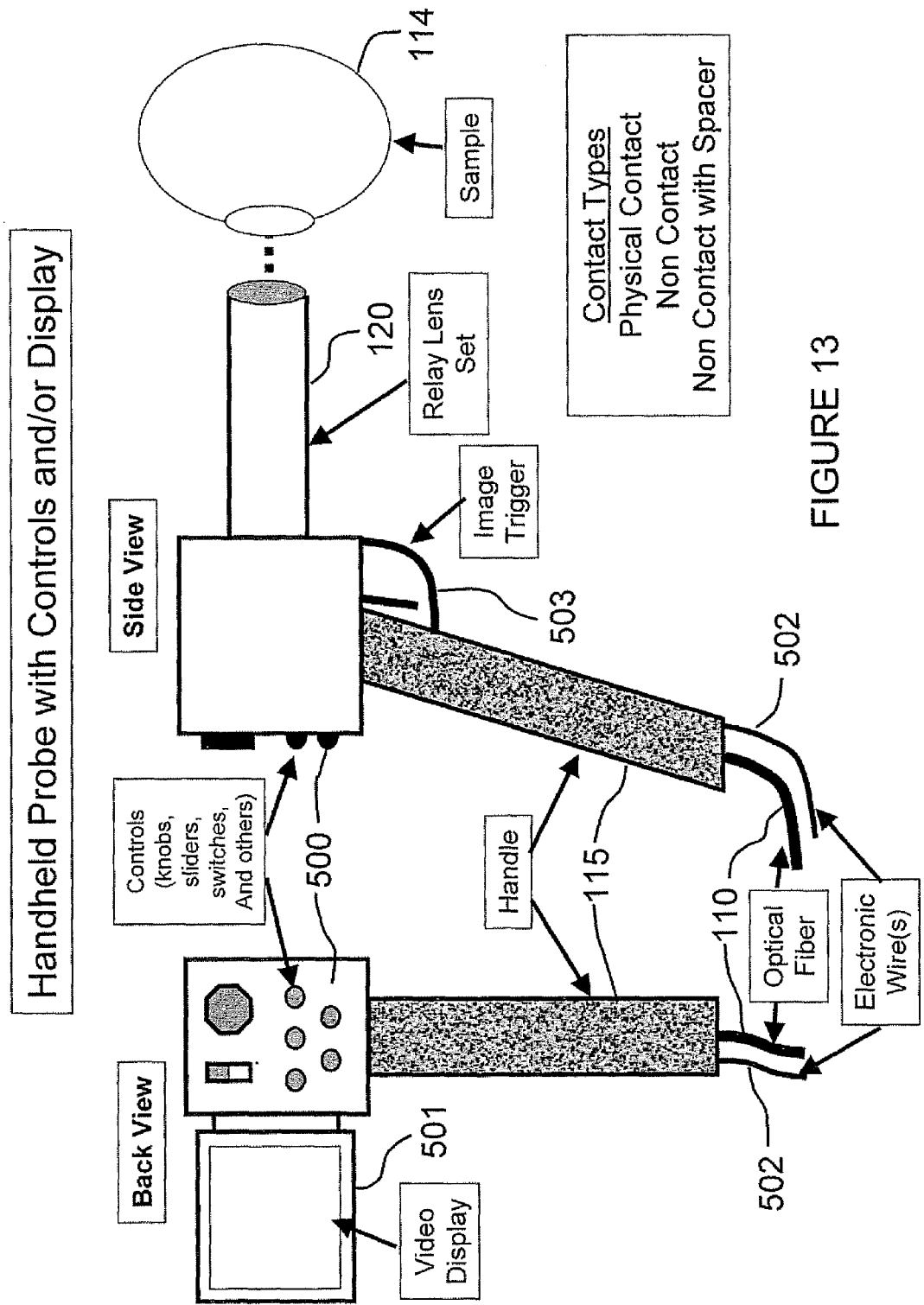
FIG. 13 is a schematic block diagram illustrating portable probes used in conjunction with controls and/or a display according to some embodiments of the present invention.

Referring now to FIG. 13, portable probes with controls and/or displays according to some embodiments of the present invention will be discussed. As illustrated in FIG. 13, the portable probe 101 has zero, one or more controls 500 and zero, one, or more video displays 501.

The controls 500 may allow the user to control the operation of the OCT engine from the probe. These controls communicate with the OCT engine via the electronic wires 502. It will be understood that although electronic wires 502 are discussed herein, communication between devices can be accomplished by any means known to those having skill in the art. For example, the controls may communicate with the OCT engine using wireless communications, such as BLUETOOTH, WiFi and the like without departing from the scope of the present invention.

One specific control is an image acquisition trigger 503. This may allow the user a one button operation to control when the system takes images of the sample. Other examples may include controls for scan pattern, scan range, scan rate, image processing options, and the like. The other addition is one or more optional video displays 501 that may be part of the portable probe. This video display would communicate with the OCT engine via the electronic wires 502. The display may illustrate real time or saved images from the sample. In addition information about the OCT system such as options, modes, and error messages may be displayed. Physically the video display 501 may, for example, be mounted substantially perpendicular to the side of the portable probe, fold out from the side of the probe, be mounted to the back of the probe (where the controls are shown in FIG. 13) or the like.

Embodiments of the present invention illustrated in FIG. 13, may include additional electronics in the portable probe that perform some of the image processing and control that typically happens in the OCT engine. For example, control of the scanning mirrors and image processing and display to support the video display. The communications with the engine could be individual analog or digital lines or more sophisticated communications such area RS-232, USB, Firewire, or Ethernet.

Figure 14:
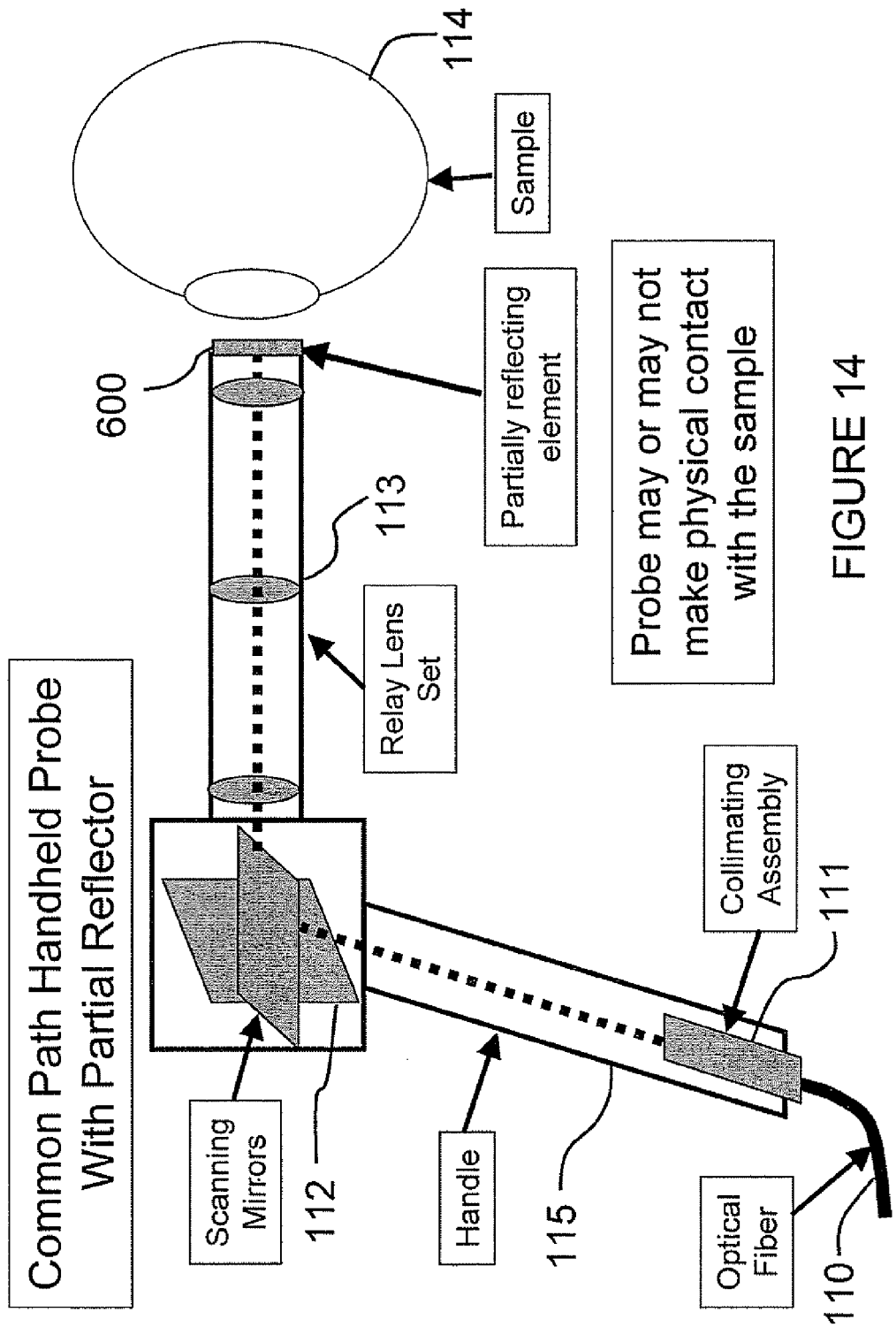
FIG. 14 is a schematic block diagram illustrating a portable probe with a common mode path design where the reflection occurs in the probe according to some embodiments of the present invention.

Referring now to FIG. 14, portable probes with a common mode path design where the reflection occurs in the probe will be discussed. A portable probe with optical fiber 110, collimating assembly 111, scanning mirrors 112, and lens relay optics 113 has already been described herein. Accordingly, the details of these elements will not be discussed farther herein. As illustrated in FIG. 14, a partially reflecting element 600 is provided at the probe tip (or otherwise placed close to the sample to be imaged), which serves as a reference reflection for a common-mode interferometer. In a common-mode interferometer, the sample and reference paths may be shared up to a point very close to the sample, so that any sources of vibration or other noise may be shared between the arms and, thus, may not affect the interferogram. The reflectance of the partially reflecting element 600 may be designed to increase the likelihood of optimal reference power on the detector so that shot-noise limited detection may be achieved. The depth of imaging beyond the reference reflection may be limited by the spectral resolution of the spectral-domain OCT system used, or by the length scan of the time domain OCT system used.

Figure 15:
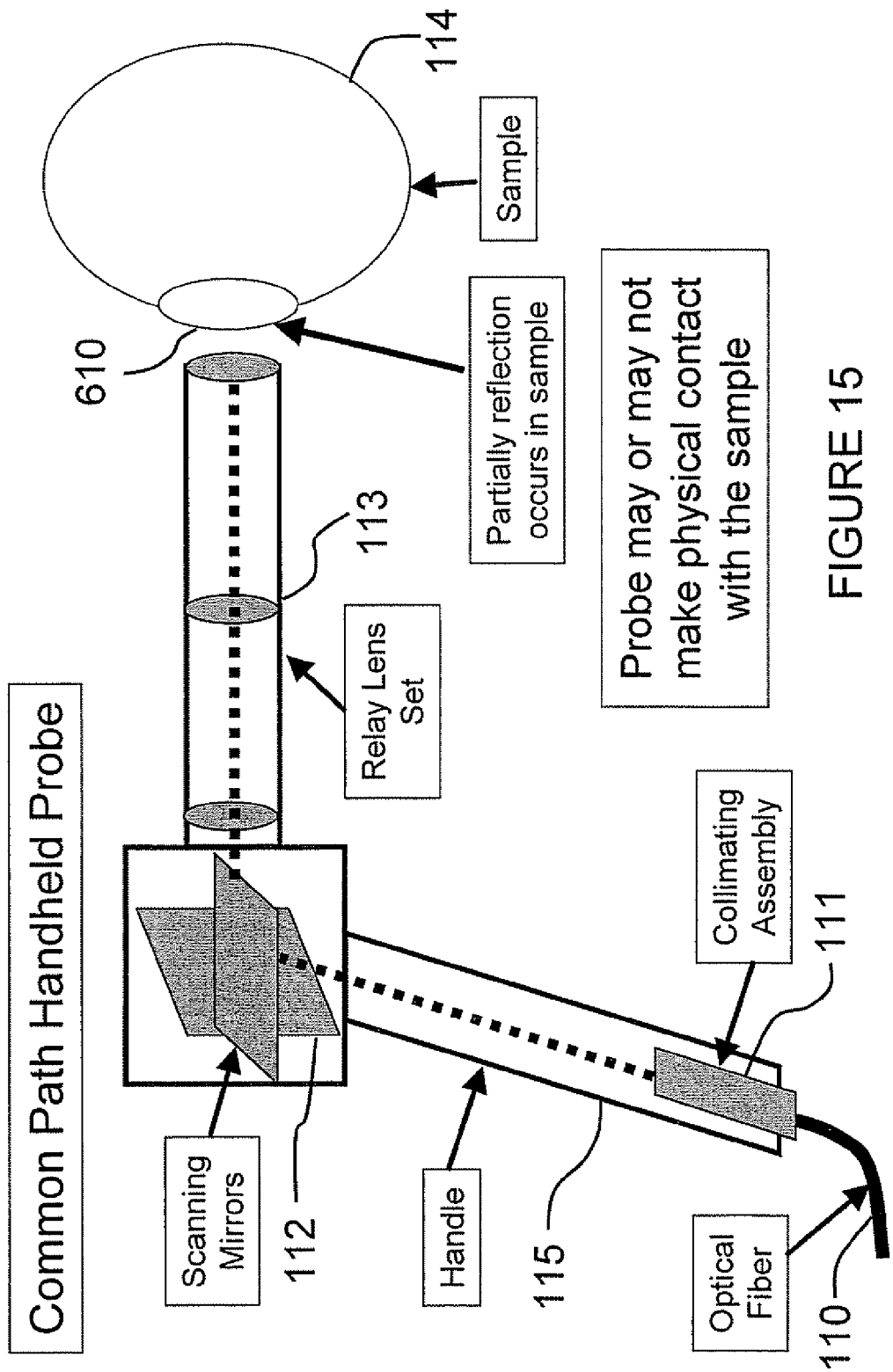
FIG. 15 is a schematic block diagram illustrating a portable probe with a common mode path design where the reflection occurs in the sample according to some embodiments of the present invention.

Referring now to FIG. 15, a portable probe with a common mode path design according to some embodiments of the present invention will be discussed. A portable probe 101 illustrated in FIG. 15 depends on reflection internal to the sample 610 itself to generate the reference reflection for common-mode interferometry. In some embodiments of the present invention, the reference reflection may be optimally close to the sample since it is inside the sample. The reflection at the surface of the sample may be used for this purpose, for example, the corneal surface reflection at the surface of the eye. In these embodiments of the present invention, the amplitude of the surface reflection may be modified to increase the likelihood of optimal detection signal to noise ration (SNR) by designing the probe optics to have a particular polarization state or incidence angle on the sample surface to generate a reflection of the desired reflectivity. The depth of imaging beyond the reference reflection may be limited by the spectral resolution of the spectral-domain OCT system used, or by the length scan of the time domain OCT system used.

Figure 16:
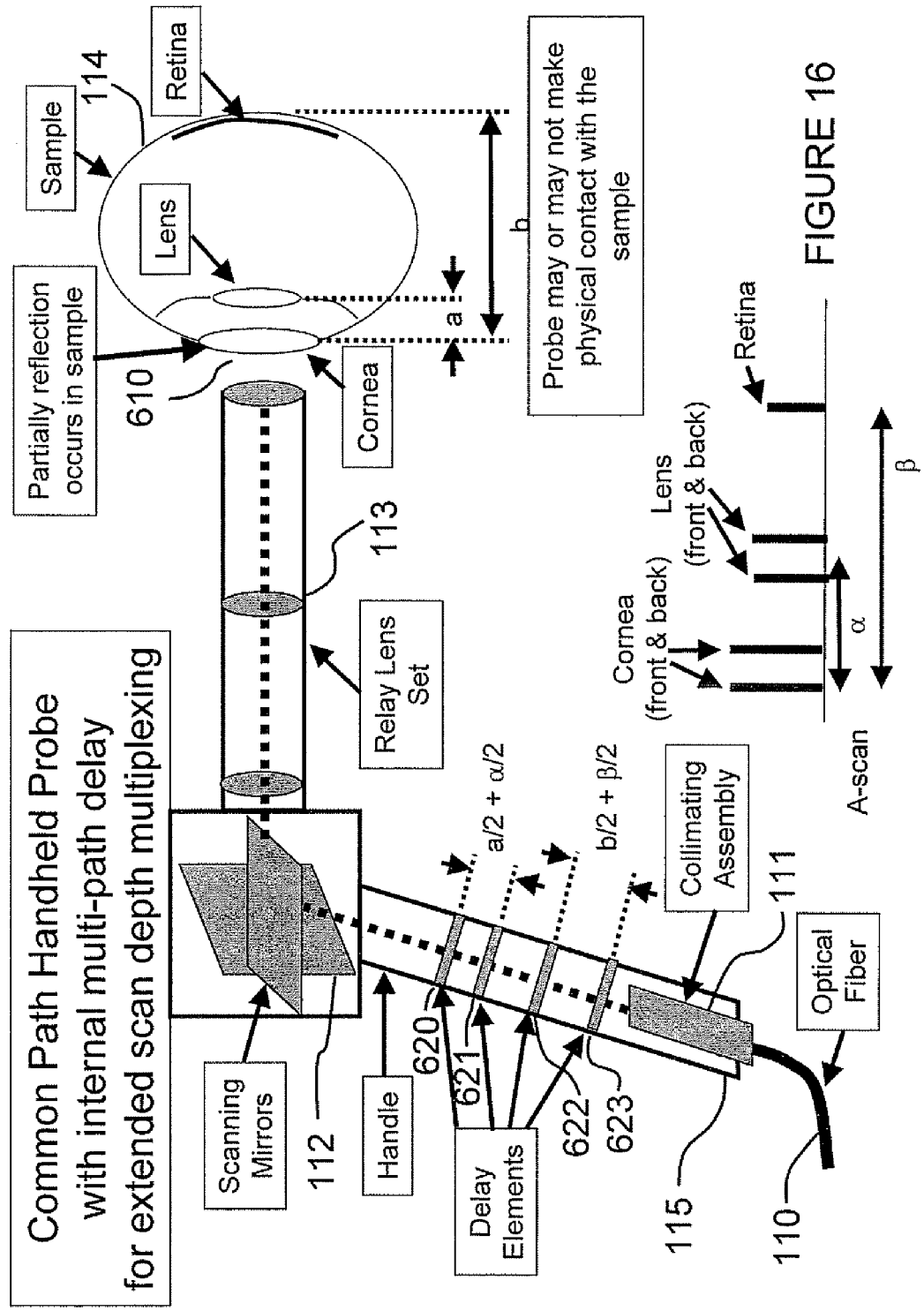
FIG. 16 is a schematic block diagram illustrating a portable probe including multi-path delay lines for extended scan depth multiplexing according to some embodiments of the present invention.

Referring now to FIG. 16, a portable probe including multi-path delay lines for extended scan depth multiplexing according to some embodiments of the present invention will be discussed. In particular, FIG. 16 illustrates a method to address possible limitations of the depth of imaging of the portable probes of FIGS. 14 and 15.

By placing a series of multi-path delay elements 620, 621, 622 and 623 in a portion of the optical path which is common to the reference and sample arms (or alternatively in the source or detector arms of the interferometer), reflections from widely varying depths within the sample may be multiplexed into the available depth scan range of the OCT system used, TDOCT or SDOCT. An example of such a multi-path delay element is a Fabry-Perot optical cavity placed in the common-mode path. The Fabry-Perot cavity may be constructed from separate reflective elements as illustrated in FIG. 16, or it may be constructed from a single optical element (e.g., a glass mirror blank) having partially reflective coatings on both sides. The length of the optical cavity may be determined by the depth of expected reflections in the sample. For example, if it is desired to perform an A-scan of the eye, in which the cornea-lens and cornea-retina optical distances are measured, two optical cavities may be used, one having a length equal one-half of the cornea-lens distance plus some offset $\alpha/2$ $((a+\alpha)/2)$, and another having a length equal to one-half of the cornea-retina distance plus some offset $\beta/2$ $((b+\beta)/2)$. The portion of the incident light which is transmitted directly through both cavities without reflection will generate A-scan reflections from the front of the cornea (located at DC) and the back of the cornea, as usual. That portion of the incident light which takes an extra round trip through the first cavity will acquire an extra group delay equal to $(a+\alpha)$, and after reflecting off of the front surface of the cornea may interfere with light reflecting off the front surface of the lens at a DC offset value of $\alpha$. Similarly, that portion of the incident light which takes an extra round trip through the second cavity may acquire an extra group delay equal to $(b+\beta)$, and after reflecting off of the front surface of the cornea may interfere with light reflecting off of the retina at a DC offset value of $\beta$. By extension of this concept, many independent reflections at arbitrary path lengths may be multiplexed into the available scan range of the OCT system used. It will be understood that additional parasitic correlations may also be generated at negative distances, and also resulting from the spacing between separate individual Fabry-Perot cavities comprising additional Fabry-Perot cavities themselves, however the correlations resulting from these parasitic cavities may be placed outside the desired imaging range by appropriate spacing of the cavities. In addition, fixed autocorrelation artifacts may be generated between internal reflections, however these latter may be remedied by assuring that the front corneal reflection dominates all other reflections by a large factor. If this cannot be achieved using a reflection within the sample itself, this same concept for multiple distance multiplexing may also be applied to the portable probe illustrated in FIG. 14 in which the reflective element may be designed specifically for this purpose.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An ophthalmic optical coherence tomography (OCT) system, comprising:
    an OCT engine including optics and electronics configured to acquire data used to generate OCT images of a subject; and
    a portable housing including a portable scanning interface device in communication with the OCT engine, comprising at least one mirror configured to scan light in at least two non-co-planar directions and at least one lens set coupled to the at least one mirror and configured to receive light from the at least one mirror, to focus the received light onto a structure of an eye of the subject, and to receive light that is scattered or reflected from the structure of the eye;
    an optical fiber connecting the housing including the portable scanning interface device to the OCT engine, the optical fiber being configured to guide light from the OCT engine to the portable scanning interface device;
    means for aligning the housing including the portable scanning interface device to the structure of the eye without using a chinrest to stabilize the subject;
    means for controlling spacing between the portable interface device and the structure of the eye without using a chinrest to stabilize the subject;
    means for setting acquisition parameters for imaging the structure of the eye;
    means for acquiring, processing and displaying volumetric OCT image data of the structure of the eye in real-time; and
    means for making the OCT images relatively insensitive to changes in the optical fiber connecting the OCT engine to the housing including the portable scanning interface device that occur during imaging without using a chinrest to stabilize the subject.

2. The system of claim 1, wherein the portable scanning interface device comprises a non-contact probe that does not make physical contact with a sample and wherein the non-contact probe further comprises a first lens set configured for the non-contact probe.

3. The system of claim 1, wherein the portable scanning interface device comprises a contact probe configured to make physical contact with a sample and wherein the contact probe further comprises a second lens set configured for the contact probe.

4. The system of claim 1, further comprising a display in the portable housing integrated with the portable scanning interface device such that the portable scanning interface device and the integrated display are configured to communicate with the OCT engine.

5. The system of claim 1, wherein the portable scanning interface device further comprises an integrated user interface in the portable housing configured to control an operation of the portable scanning interface device in communication with the OCT engine.

6. The system of claim 1, wherein the means for making the OCT images relatively insensitive to changes in the optical fiber connecting the OCT engine to the housing including the portable scanning interface comprises a reference arm and a sample arm sharing a single fiber.

7. An ophthalmic optical coherence tomography (OCT) system, the system comprising:
    an OCT engine; and
    a portable housing including a portable scanning interface device and an integrated display, the portable housing including the portable scanning interface device being connected to the OCT engine by at least an optical fiber and including means for making an OCT image acquired by the system relatively insensitive to changes occurring during imaging in the at least one optical fiber connecting the portable housing to the OCT engine;
    wherein the means for making an OCT image acquired by the system relatively insensitive to changes does not include the use of a chinrest to stabilize a subject; and
    wherein the means for making an OCT image acquired by the system relatively insensitive to changes comprises an integrated reference arm wherein a sample arm and the reference arm share a single fiber to substantially reduce distortion.

8. The OCT system of claim 7, wherein the portable scanning interface device further comprises a user interface configured to control an operation of the OCT engine in communication with the portable scanning interface device.

9. The OCT system of claim 8, wherein the operation comprises at least one of triggering an image acquisition, controlling a scan pattern, controlling a scan rate, and controlling an image processing option, the user interface comprising:
    an image acquisition trigger configured to acquire images of the sample; and
    at least one control configured to adjust a scan pattern, a scan range, a scan rate and/or image processing options.

10. The OCT system of claim 7, wherein the display is configured to illustrate at least one of a real time image of the sample, a saved image of the sample, a system option, a system mode, and a system error message.

11. The OCT system of claim 7, wherein the integrated display is configured to be mounted substantially perpendicular to the side of the portable scanning interface device, fold out from the side of the portable scanning interface device, or be mounted to the back of the portable scanning interface device.

12. An ophthalmic optical coherence tomography (OCT) system comprising:
- a portable housing including a portable scanning interface device and a reference arm integrated with the portable scanning interface device, the portable scanning interface device and the integrated reference arm being configured to communicate with an OCT engine,
- wherein the system further comprises a means for substantially reducing distortion of a resulting image; and
- wherein the means for substantially reducing distortion comprises the integrated reference arm sharing a single fiber with a sample arm of the system.

13. The system of claim 12, wherein the portable scanning interface device comprises a beamsplitter configured to receive light and provide a portion of the light to an optical path of the reference arm of the portable scanning interface device and provide a remaining portion of the light to an optical path of the sample.

14. The system of claim 13, wherein the beamsplitter is further configured to receive light from the optical path of the reference arm of the portable scanning interface device and the optical path of the sample, recombine the light from the optical path of the reference arm and the optical path of the sample and provide the recombined light to an OCT engine in communication with the portable scanning interface device for processing.

15. An ophthalmic optical coherence tomography imaging System comprising:
- an optical engine and an optical fiber in connection with the optical engine;
- a display configured for real-time display of optical coherence tomography images and positioned in a portable housing; and
- a portable scanning interface device configured to align to a subject without repositioning the subject, the portable scanning interface device being provided in the portable housing, the portable housing further comprising:
  - a connection to the optical fiber that is in connection with the optical engine;
  - a collimator assembly configured to receive light from the optical fiber;
  - at least one mirror configured to scan light directed from the collimator assembly in at least two noncoplanar directions; and
  - at least one lens set configured to focus light from the at least one mirror configured to scan at least two noncoplanar directions onto a structure of an eye of the subject, and to receive light that is scattered from the structure of the eye,
- wherein the system further comprises a means for substantially reducing distortion of a resulting image; and
- wherein the means for substantially reducing distortion comprises the integrated reference arm sharing a single fiber with a sample arm of the system.

16. The system of claim 15:
- wherein the at least one lens set of the portable scanning interface device does not make physical contact with the subject; and
- wherein the at least one lens set further comprises a lens set configured for non-contact imaging of the subject eye.

17. The system of claim 15:
- wherein the at least one lens set of the portable scanning interface device is configured to make physical contact with the subject; and
- wherein the at least one lens set further comprises a lens set configured for imaging the subject eye.

18. The system of claim 15, wherein the portable scanning interface device is further configured to receive at least two different lens sets.

19. The system of claim 18:
- wherein the portable scanning interface device is configured to receive one of the at least two lens sets;
- wherein at least one of the at least two lens set is configured to image a retina; and
- wherein at least one of the at least two lens set is configured to image a cornea.

20. The system of claim 18:
- wherein the portable scanning interface device is configured to receive one of the at least two lens sets;
- wherein at least one of the at least two lens set is configured to image a sample without making physical contact with the sample; and
- wherein at least one of the at least two lens set is configured to image a sample with making physical contact with the sample.

21. The system of claim 15, wherein the portable scanning interface device further comprises:
- an integrated reference arm comprising a beamsplitter configured to receive light and provide a portion of the light to an optical path of the reference arm and a remaining portion of the light to the at least one mirror configured to scan light in at least two noncoplanar directions onto a structure of the eye.

22. The system of claim 15, wherein the real-time display and the portable scanning interface device are integrated into a single cohesive unit.

23. The system of claim 15, wherein the portable scanning interface device further comprises a user interface configured to control an operation of an OCT engine in communication with the portable scanning interface device, wherein an operation includes at least one of triggering an image acquisition, controlling a scan pattern, controlling a scan rate, and controlling an image processing option.

24. An ophthalmic optical coherence tomography (OCT) system, comprising:
- an OCT engine including optics and electronics configured to acquire data used to generate OCT images of a subject; and
- a portable housing including a portable scanning interface device in communication with the OCT engine, comprising at least one mirror configured to scan light in at least two non-co-planar directions and at least one lens set coupled to the at least one mirror and configured to receive light from the at least one mirror, to focus the received light onto a structure of an eye of the subject, and to receive light that is scattered or reflected from the structure of the eye;
- an optical fiber connecting the housing including the portable scanning interface device to the OCT engine, the optical fiber being configured to guide light from the OCT engine to the portable scanning interface device;
- means for handheld imaging of a structure of the eye in at least two non-co-planar directions, the means comprising:
- means for aligning the housing including the portable scanning interface device to the structure of the eye without using a chinrest to stabilize the subject; and
- means for controlling spacing between the portable interface device and the structure of the eye without using a chinrest to stabilize the subject.

25. The system of claim 24 further comprising
- means for setting acquisition parameters for imaging the structure of the eye;

means for acquiring, processing and displaying OCT image data of the structure of the eye in real-time; and means for making the OCT images relatively insensitive to changes in the optical fiber connecting the OCT engine to the housing including the portable scanning interface device that occur during imaging without using a chinrest to stabilize the subject.

26. The system of claim 24, further comprising a display in the portable housing integrated with the portable scanning interface device such that the portable scanning interface device and the integrated display are configured to communicate with the OCT engine.

27. The system of claim 24, wherein the portable scanning interface device further comprises an integrated user interface in the portable housing configured to control an operation of the portable scanning interface device in communication with the OCT engine.

* * * * *

UNITED STATES PATENT AND TRADEMARK OFFICE
CERTIFICATE OF CORRECTION

PATENT NO. : 8,064,989 B2
APPLICATION NO. : 11/535663
DATED : November 22, 2011
INVENTOR(S) : Brown et al.

It is certified that error appears in the above-identified patent and that said Letters Patent is hereby corrected as shown below:

In the Patent:
Column 1, Line 25: Please correct "quickly generated Since OCT"
  to read -- quickly generated. Since OCT --
Line 38: Please correct "like a findus camera"
  to read -- like a fundus camera --

Column 2, Line 19: Please correct "a beam splitter" to read -- a beamsplitter -- and
  please correct "The beam splitter" to read -- The beamsplitter --

Column 8, Line 11: Please correct "optical fiber 110" to read -- optical fiber 110. --

In the Claims:
Column 15, Claim 15, Line 29: Please correct "System comprising:"
  to read -- system comprising: --

Signed and Sealed this
Twenty-eighth Day of February, 2012

David J. Kappos
*Director of the United States Patent and Trademark Office*